United States Patent [19]

Higley

[11] Patent Number: 5,180,845

[45] Date of Patent: Jan. 19, 1993

[54] THERMALLY STABLE, FLUORINE-CONTAINING ORGANSILANES

[75] Inventor: David P. Higley, Wilmington, Del.

[73] Assignee: E. I. Du Pont de Nemours and Company, Wilmington, Del.

[21] Appl. No.: 864,954

[22] Filed: Apr. 7, 1992

[51] Int. Cl.$^5$ .............................. C07F 7/08; C07F 7/18
[52] U.S. Cl. ................................. 556/445; 428/391; 428/405
[58] Field of Search ............... 556/445; 428/391, 405

[56] References Cited

U.S. PATENT DOCUMENTS

| | | | |
|---|---|---|---|
| 3,304,320 | 2/1967 | Spencer | 260/448.2 |
| 3,328,348 | 6/1967 | Sporck | 260/46.5 |
| 3,642,596 | 2/1972 | Takamizana et al. | 204/158 |
| 3,692,843 | 9/1972 | Resnick | 260/615 A |
| 4,031,119 | 6/1977 | Ponomarev et al. | 260/448.2 B |
| 4,489,201 | 12/1984 | von Au et al. | 556/445 X |
| 4,900,474 | 2/1990 | Terae et al. | 556/445 X |
| 4,996,344 | 2/1991 | Inomata et al. | 556/445 UX |
| 5,099,053 | 3/1992 | Takaoka et al. | 556/445 UX |

Primary Examiner—Paul F. Shaver
Attorney, Agent, or Firm—Paul R. Steyermark

[57] ABSTRACT

A class of organosilanes of the general formula

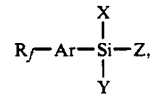

wherein Ar is a divalent aromatic radical; $R_f$ is a defined fluoroalkyl or perfluoroalkyl ether group; X is methyl, $R_fAr$ as defined above, a halogen other than fluorine, or an alkoxy group; and each one of Y and Z is a halogen other than fluorine or an alkoxy group. These organosilanes are very useful as precursors to polysiloxane coupling agents for bonding fluoropolymers to glass fibers which can withstand the usual fluoropolymer melt-processing temperatures without decomposition.

9 Claims, No Drawings

THERMALLY STABLE, FLUORINE-CONTAINING ORGANSILANES

BACKGROUND OF THE INVENTION

This invention relates to a class of novel organosilanes which are useful, among others, as precursors for coupling agents for improving the adhesion of fluoropolymers in coatings, laminates, and composites. Certain members of this class also are suitable as the stationary phase in both gas and liquid chromatography. Other potential uses for these organosilanes include the preparation of high-stability silicone fluids and elastomers.

Various organosilicon compounds, including fluorine-containing organosilanes, are known. For example, U.S. Pat. No. 4,031,119 to Ponomarev et al. discloses certain perfluoroalkyl(alkoxyphenyl)methyldichlorosilanes, which are made by treating a perfluoroalkyl(alkoxy)bromobenzene with magnesium and then contacting the resulting perfluoroalkyl(alkoxy)magnesium bromobenzene with a trifunctional silane.

U.S. Pat. No. 3,328,348 to Sporck discloses polyorganosiloxanes containing at least one trifluoromethyl-substituted phenyl group.

U.S. Pat. No. 2,884,433 to Kohl discloses certain trifluoromethylphenylsilanes, which are made by a reaction of the corresponding Grignard reagent from trifluoromethylphenyl bromide with silicon tetrachloride.

Organosilicon compounds have great potential both as intermediates, because of the hydrolytic instability and reactivity of many types of covalent silicon bonds with atoms such as, for example, oxygen in compounds containing the Si—O—C group, and halogen other than fluorine, and as the final products because of their thermal stability and of low chemical reactivity of covalent silicon bonds with atoms such as, for example, silicon, carbon belonging to certain organic groups, fluorine, and oxygen in compounds containing the Si—O—Si group.

SUMMARY OF THE INVENTION

According to the present invention, there is now provided a class of organosilanes having the following formula (1):

$$R_f\text{—Ar—}\underset{\underset{Y}{|}}{\overset{\overset{X}{|}}{Si}}\text{—Z} \quad (1)$$

where $R_f$ has a maximum of 18 carbon atoms and is selected from the group consisting of
(a) perfluoroalkyl groups having at least 4 carbon atoms
(b) —[CF$_2$CF(CF$_3$)O]$_n$—CF$_2$—CF$_2$—CF$_3$, where n is an integer of at least 1;
(c) —CF$_2$—(CF$_2$—O)$_m$—CF$_3$, where m is an integer of at least 2; and
(d) —CH$_2$—C(CF$_3$)$_2$—CF$_2$—CF$_2$—CF$_3$;
Ar is a divalent aromatic radical;
X is selected from the group consisting of
(e) methyl;
(f) $R_f$—Ar, where each of $R_f$ and Ar is as defined above;
(g) halogen atoms selected from the group consisting of chlorine, bromine, and iodine; and
(h) alkoxy groups; and
each of Y and Z independently is selected from the group consisting of
(i) halogen atoms selected from the group consisting of chlorine, bromine, and iodine; and
(j) alkoxy groups.

DETAILED DESCRIPTION OF THE INVENTION

Ar in formula (1), above, can be any divalent aromatic radical, as this term is understood in the art, including those containing the classic six-, ten-, and fourteen-carbon aromatic rings, including, for example, radicals remaining when two ring hydrogen atoms are removed from an aromatic compound such as benzene, naphthalene, toluene, xylene, and anthracene, or from a five-membered or six-membered heterocyclic ring containing oxygen or nitrogen atoms such as, for example, furan, pyrrole, and pyridine.

The $R_f$ group can be, i.a., a fluoroalkyl or perfluoroalkyl group, which can be either normal or branched, and preferably has more than four carbon atoms, especially more than six carbon atoms. Normal perfluoroalkyl groups include, for example, perfluorobutyl, perfluoropentyl, perfluorohexyl, perfluorodecyl, perfluorododecyl, and perfluorooctadecyl. Organosilanes of formula (1) where $R_f$ has more than eighteen carbon atoms are considered less practical to make, although such organosilanes would be perfectly suitable in all applications contemplated for this class of compounds. A typical suitable branched fluoroalkyl group is —CH$_2$—C(CF$_3$)$_2$—CF$_2$—CF$_2$—CF$_3$.

The $R_f$ groups also can be certain perfluoro[(alkyleneoxy)alkyl] radicals. These include perfluoro[methylene(polymethyleneoxy)methyl] radicals (c) and perfluoro[(polyisopropyleneoxy)propyl] radicals (b). The number of repeating perfluoroalkyleneoxy groups preferably is 3 or more in each case.

Typical alkoxy groups according to definition (h) of X and definition (j) of Y and Z are methoxy and ethoxy groups and normally will be lower alkoxy groups of up to 4 carbon atoms.

Upon hydrolysis, the compounds of formula (1), above, afford polysiloxanes.

Methods have been developed for the preparation of compounds of formula (1), as described herein. These compounds are precursors to the corresponding polysiloxanes which are very useful, i.a., as coupling agents, or adhesion promoters, for bonding fluoropolymers to glass fibers. Typically, for such purposes, a hydrolysis mixture of a precursor organosilane is applied to glass fibers, which then are dried, chopped and mixed with any of a variety of fluoropolymers during melt extrusion. When used in this manner, the compounds of the present invention yield polysiloxanes that provide a stronger interaction with fluoropolymers than do similar compounds having only 1-3 fluorinated carbon atoms. Although other silanes are known in the art which bear four or more fluorinated carbon atoms, those silanes contain an aliphatic linkage between the silicon atom and the fluorocarbon chain, which appears to be responsible for their lack of adequate thermal stability at the high temperatures, in excess of 320° C., normally required in melt processing fluoropolymers. By contrast, coupling agents derived from the compounds of the present invention are stable at such high melt processing temperatures.

This invention is now illustrated by the following examples of certain representative embodiments thereof, wherein all data obtained in units other than SI have been converted to SI units.

EXAMPLE 1

Preparation of 1-bromo-4-perfluorohexylbenzene

A 500-ml three-necked flask fitted with a mechanical stirrer, reflux condenser/gas inlet, and thermometer was charged in an argon atmosphere with 156.08 g (0.35 mole) of n-perfluorohexyl iodide, 47.66 g (0.75 mole) of copper powder freshly prepared by a reaction of aqueous cupric sulfate with zinc dust, and 350 ml of reagent grade dimethyl sulfoxide. The mixture was heated with stirring at 100°-105° C. for 1.5 hours. The resulting solution of perfluorohexylcopper was cooled to 25° C., and to it was added 84.87 g (0.300 mole) of 1-bromo-4-iodobenzene. The mildly exothermic reaction was maintained at 30° C. by cooling in a water bath; the mixture was then left stirring overnight at room temperature.

The resulting mixture was extracted with several portions of methyl t-butyl ether; the combined extracts were washed with water and dried over magnesium sulfate. After the solvent was removed at a reduced pressure, the residue was further distilled at a reduced pressure to give 118.6 g (0.250 mole, 83% yield) of 1-bromo-4-perfluorohexylbenzene boiling at 72°-74° C./266 Pa.

In the same way were prepared 1-bromo-4-perfluorooctylbenzene (b.p. 98°-100° C./246 Pa) and 1-bromo-4-perfluorobutylbenzene (b.p. 50° C./266 Pa).

EXAMPLE 2

Preparation of (4-perfluorohexylphenyl)methyldichlorosilane

A 100-ml three-necked flask, equipped with a mechanical stirrer, low-temperature thermometer, gas inlet, and a 25-ml dropping funnel was flushed with argon, then charged with 11.4 g (24 mmoles) of 1-bromo-4-perfluorohexylbenzene and 50 ml of diethyl ether. To the stirred contents of the flask, there was added from the dropping funnel 16.1 ml of 1.55M n-butyllithium in hexane (25 mmoles) over a period of 20 minutes at −30° C.

In an inert atmosphere, a solution was prepared from 6.456 g (25 mmoles) of magnesium bromide etherate and 12 ml of diethyl ether and was transferred by syringe to the dropping funnel. Beginning 15 minutes after completion of the n-butyllithium addition, this solution was introduced into the stirred contents of the flask, still at −30° C., over a period of 10 minutes. The reaction mixture was then cooled to about −75° C., and 5.38 g (36 mmoles) of methyltrichlorosilane was added to it rapidly. Beginning 10 minutes after this addition, the reaction mixture was allowed to warm gradually to room temperature.

Ether was removed by distillation from the product mixture and was replaced by 1,1,2-trichloro-1,2,2-trifluoroethane (TCTFE). The resulting mixture was filtered at room temperature in an inert atmosphere; the solvent was distilled from the filtrate at normal pressure, and the residue was distilled under vacuum to give 4.7 g (9.2 mmoles, 38% yield) of (4-perfluorohexylphenyl)methyldichlorosilane, boiling at 72° C./45 Pa.

EXAMPLE 3

Preparation of (4-perfluorooctylphenyl)trimethoxysilane

A 3-l four-necked flask equipped with a mechanical stirrer, a gas inlet connected to an argon bubbler, a low-temperature thermometer, and an addition funnel was flushed with argon and charged with 320 g (0.556 mole) of 4-perfluorooctyl-1-bromobenzene in 1 liter of anhydrous ether. The flask was cooled to −30° C. in an ice-methanol bath, while the solution was stirred. The addition funnel was charged under argon with 361 ml of a 1.55M solution of n-butyllithium (0.560 mole) in hexane, which then was added to the contents of the flask at such a rate that the temperature of the contents did not exceed −25° C. The addition funnel next was charged with a solution of magnesium bromide made from the reaction of 105.2 g (0.560 mole) of ethylene bromide in ether with 14.59 g (0.600 mole) of magnesium turnings. This magnesium bromide solution was added at −30° C. to the stirred contents of the flask during a 1.5 hour period.

Thirty minutes following the completion of this addition, the reaction mixture was cooled to −74° C. in an acetone/dry ice bath. Tetramethoxysilane, 127.9 g (0.84 mole) was added rapidly with stirring, and the mixture was allowed to warm to room temperature overnight. A portion of the supernatant liquid was decanted under argon; the solids in the flask were repeatedly washed by decantation and filtration with methylene chloride under argon. Ether was distilled from the combined organic liquids to leave a solution in methylene chloride along with some additional solids.

This procedure was repeated starting with 381.8 g (0.664 mole) of 4-perfluorooctyl-1-bromobenzene. The combined product solutions were filtered under argon, and solvent was removed from the filtrate at a reduced pressure. Final distillation gave 570 g (0.925 mole) of (4-perfluorooctylphenyl)trimethoxysilane boiling at 92°-95° C./266 Pa (76% yield).

EXAMPLE 4 (COMPARATIVE)

Preparation of (4-trifluoromethylphenyl)trimethoxysilane

A 2-l three-necked flask equipped with a mechanical stirrer, an addition funnel, a low-temperature thermometer, and a gas inlet connected to an argon bubbler was flushed with argon and charged with 87.1 g (0.387 mole) of 4-bromobenzotrifluoride dissolved in 750 ml of anhydrous diethyl ether. The flask contents were cooled to −30° C. The addition funnel was charged with 242 ml of a 1.6M solution of n-butyllithium (0.387 mole) in hexane. This was added to the flask with stirring during a 45-minute period at a temperature of −25° to −30° C. Thirty minutes after the completion of this addition, the flask was cooled further to −75° C. in a dry ice/acetone bath. Tetramethoxysilane, 78.6 g (0.516 mole) was added in one portion to the rapidly stirred flask contents. The reaction mixture was then allowed to warm to room temperature during a period of one hour.

The mechanical stirrer and addition funnel were replaced by a magnetic stirrer and a still head. About two-thirds of the ethyl ether was distilled off and replaced by an equal volume of TCTFE. Most of the remaining ether was removed by further distillation. The remaining solution was cooled to room temperature, diluted with additional TCTFE, and filtered under nitrogen. Solvent was removed from the filtrate under reduced pressure; the oily residue was distilled to give 73.9 g (0.277 mole, 72% yield) of (4-trifluoromethylphenyl)trimethoxysilane boiling at 69.5°–71° C./266 Pa.

EXAMPLE 5

Preparation of {4-[3,3,4,4,5,5,5-heptafluoro-2,2-bis(trifluoromethyl)-pentyl]phenyl}trimethoxysilane A 500-ml three-necked flask equipped with a mechanical stirrer, a gas inlet, a low-temperature thermometer, and an addition funnel was flushed with argon. Argon atmosphere was subsequently maintained throughout the reaction. The flask was charged with a solution of 48.9 g (0.100 mole) of 4-[3,3,4,4,5,5,5-heptafluoro-2,2-bis(trifluoromethyl)pentyl]-1-bromobenzene in 300 ml of anhydrous diethyl ether. The addition funnel was charged with 62.5 ml of a 1.60M solution of n-butyllithium (0.100 mole) in hexane, which was then added dropwise to the stirred contents of the flask during a 45-minute period at −25° to −30° C. The addition funnel was recharged with a solution of 25.8 g (0.100 mole) of magnesium bromide etherate in 50 ml of anhydrous ethyl ether. Beginning 15 minutes after the end of the addition of n-butyllithium, this solution was added to the reaction mixture at −25° to −30° C. during a period of 30 minutes. The reaction mixture was maintained at −30° C. for an additional period of 30 minutes, then cooled to −75° C., whereupon 19.0 g (0.125 mole) of tetramethoxysilane was added in one portion with rapid stirring.

The reaction mixture was worked up as described in Example 4. The desired reaction product, {4-[3,3,4,4,5,5,5-heptafluoro-2,2-bis(trifluoromethyl)-pentyl]phenyl}trimethoxysilane, boiling at 82°–84° C./39 Pa, was obtained in a yield of 36.7 g (69%).

EXAMPLE 6

Silane hydrolysis and coating experiments

Each of (4-perfluorooctylphenyl)trimethoxysilane (Run 1) and (4-trifluoromethylphenyl)trimethoxysilane (Run 2) were hydrolyzed by stirring 1 ml of each compound for 4 hours at room temperature with 36 ml of isopropyl alcohol, 0.6 ml of acetic acid, and 1.9 ml of deionized water. Each mixture was then diluted with 36 ml of additional isopropyl alcohol and was dip-coated on a glass slide. In each case, the contact angle for water and for hexadecane was determined by the sessile drop method, both as made and after a warm water rinse. The method is described in A. W. Adamson, *Physical Chemistry of Surfaces*, Fourth Edition, John Wiley and Sons, New York, 1982, pp. 341 ff.

Hydrocarbon repellency is a useful property in applications where resistance to soiling by oily substances is desired, for example, in coatings applied for the protection of statuary. High hydrocarbon contact angle also indicates the presence of fluorocarbon on the surface, which is desired for improved compatibility with fluoropolymers. Many methyl- or phenyl-substituted polysiloxanes on a glass surface will give high water contact angles but not high hydrocarbon contact angles.

The following results were obtained, where standard deviation is given in parentheses:

TABLE 1

| | Run 1 | | | |
|---|---|---|---|---|
| | Contact Angle | | | |
| | Water | | Hexadecane | |
| | Adv[1] | Rec[2] | Adv[1] | Rec[2] |
| As made | 113(4) | 92(2) | 73(2) | 57(6) |
| After rinse | 119(3) | 88(3) | 68(2) | 55(4) |

[1]Advancing.
[2]Receding

TABLE 2

| | Run 2 | | | |
|---|---|---|---|---|
| | Contact Angle | | | |
| | Water | | Hexadecane | |
| | Adv[1] | Rec[2] | Adv[1] | Rec[2] |
| As made | 100(1) | 75(1) | 41(3) | 31(2) |
| After rinse | 99(1) | 69(1) | 38(2) | 27(1) |

[1]Advancing.
[2]Receding

The above results show the effect of longer fluorocarbon chain length on contact angles of water and hexadecane (advancing and receding). While many organosilanes are hydrophobic, and therefore the differences in contact angles of water are not very large, the effect of chain length on hexadecane contact angle is particularly significant. This can be represented in yet another table, as the $C_8F_{17}/CF_3$ contact angle ratios:

TABLE 3

| | $C_8F_{17}/CF_3$ Contact Angle Ratio | | | |
|---|---|---|---|---|
| | Water | | Hexadecane | |
| | Adv[1] | Rec[2] | Adv[1] | Rec[2] |
| As made | 1.13 | 1.23 | 1.78 | 1.84 |
| After rinse | 1.20 | 1.28 | 1.79 | 2.04 |

[1]Advancing.
[2]Receding

EXAMPLE 7

Single-fiber determination of effective shear strength

Selected organosilanes were tested as coupling agents for glass fibers. Critical length determinations were made using the method of W. A. Fraser et al., *SPI 30th Annual Tech Conf. Reinf. Plast.*, 22-A (1975). Untreated, 13-micrometer diameter commercial glass fibers (from Owens-Corning Fiberglass) were dipped in silane hydrolysis solutions, dried, and cured at 110° C.; then embedded in a tetrafluoroethylene/perfluoro(propyl vinyl ether) copolymer (Du Pont, Teflon ® PFA 340) by pressing between two 203-micrometer thick sheets of a film of that fluoropolymer at a pressure of 13790 kPa, while heating at 340° C. In this test, the film and the fiber imbedded therein are stretched along the fiber axis. While the film itself stretches, the fiber breaks and continues breaking as long as the adhesion of the fiber to the film is large enough to cause breakage of the fiber before the fiber slips within the fluoropolymer sheets. The average length of the broken fiber fragments can be used as a measure of adhesion. The results are correlated with the effective shear strength, as taught in the above Fraser et al. reference.

The following results were obtained:

TABLE 4

| Run | Organosilane | Effect. shear strength, kPa |
|---|---|---|
| 1 | None (control) | 14775 |

TABLE 4-continued

| Run | Organosilane | Effect. shear strength. kPa |
| --- | --- | --- |
| 2 | $CF_3C_6H_4Si(OCH_3)_3$ | 21022 |
| 3 | $C_4F_9C_6H_4Si(OCH_3)_3$ | 20594 |
| 4 | $C_6F_{13}C_6H_4Si(OCH_3)_3$ | 27634 |
| 5 | $C_8F_{17}C_6H_4Si(OCH_3)_3$ | 28751 |

It can be seen that, while an increase of the perfluoroalkyl chain from one carbon to four carbons does not cause any improvement of the effective shear strength, a further increase of the chain length to six carbon atoms causes a dramatic improvement of the effective shear strength, which is further slightly improved when the chain length is increased to eight carbon atoms.

EXAMPLE 8

Determination of the thermal stabilities of polysiloxanes

The thermal stabilities of the silica-supported polysiloxanes derived from a variety of trialkoxysilanes were determined in the following manner:

In a small polyethylene ampule were combined 100 mg of fumed silica (Cabosil MS-7, Cabot Corp.), 0.200 mmole of silane, and 1.0 ml of a solution prepared from 7.60 g of isopropyl alcohol, 2.00 g of water, and 0.40 g of formic acid. The ampule was suspended in an ultrasonic cleaning bath, and the hydrolysis mixture was subjected to sonication at room temperature during 2.5 hours. The mixture was transferred to a glass vial; the liquid was evaporated in a stream of nitrogen; and the white solid residue was dried and cured overnight at 120° C. in a vacuum oven. A sample of the resulting silica-supported polysiloxane was subjected to thermogravimetric analysis (TGA) using a Du Pont Model 1090 TGA instrument, heating under nitrogen at a rate of 10° C./min to about 650° C. or until no further weight loss was observed. The results of these tests are given below in Table 5, where the decomposition temperature, Td, is the temperature at which 10% of total weight loss has occurred. The starting silanes had the formula $R'—Si(O—R)_3$, where R was methyl or ethyl and R' was varied as shown. In runs 1-3 and 10, commercial silanes were employed as starting materials, while in the remaining runs, laboratory-made silanes were employed.

TABLE 5

| Run No. | R' | Td, °C |
| --- | --- | --- |
| 1 | $(CF_3)_2CF—OCH_2CH_2CH_2—$ | 304 |
| 2 | $CF_3(CF_2)_5—CH_2CH_2—$ | 313 |
| 3 | $CF_3—CH_2CH_2—$ | 328 |
| 4 | $CF_3(OCF_2)_3—OCF_2CF_2—C_6H_4—$ | 382 |
| 5 | $CF_3CF_2CF_2—[OCF(CF_3)CF_2]_3—C_6H_4—$ | 409 |
| 6 | $CF_3CF_2CF_2—C(CF_3)_2—CH_2—C_6H_4—$ | 430 |
| 7 | $CF_3(CF_2)_5—C_6H_4—$ | 447 |
| 8 | $CF_3(CF_2)_7—C_6H_4—$ | 458 |
| 9 | $CF_3—C_6H_4—$ | 463 |
| 10 | $C_6H_5—$ | 488 |

The above table shows that polysiloxanes derived from silanes in which a fluoroalkyl or fluoroalkoxy substituent is attached to silicon by means of an aliphatic (alkylene) group, as in runs 1-3, have lower thermal stability than those attached through an aromatic (phenylene) group, such as those in runs 4-8. The former type, when used for the treatment of glass fibers to improve bonding of those fibers to a fluoropolymer matrix will not have adequate thermal stability within the normal temperature range of 320°-340° C. employed for fluoropolymer processing. By contrast, the polysiloxanes made from the organosilanes of the present invention, runs 5-8, which are stable at those temperatures, can be reasonably expected to be effective bonding agents under those conditions. The polysiloxanes of runs 9 and 10, shown for comparison, also have sufficient thermal stability to be usable at those elevated temperatures; however, they lack sufficient compatibility with fluoropolymer resins to function as effective bonding agents.

EXAMPLE 9

Preparation of perfluoroalkylether(4-bromophenyl)ketones

These ketones were prepared in the general manner described by L. S. Chen and C. Tamborski, in J. Fluorine Chem., 19, 43 (1981). In a one-liter three-necked round-bottom flask, equipped with a stirrer, thermometer, and addition funnel, were combined under nitrogen 11.41 g (0.484 mole) of 1,4-dibromobenzene and 450 ml of anhydrous ethyl ether. The flask was cooled with a dry ice/acetone bath, and the addition funnel was charged with 30 ml of a 1.6M solution of n-butyllithium (0.048 mole) in hexane. This reagent was added dropwise to the stirred contents of the flask, at −74° to −78° C., during a period of 40 minutes. The addition funnel was then charged with a solution in ether (ca. 30 ml) of 35.5 g of a mixture of ethyl esters derived from an oligomer of hexafluoropropylene oxide, consisting of $R_fCO_2Et$ where $R_f$ had the following formula (2)

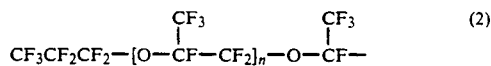

$$CF_3CF_2CF_2—[O—\overset{CF_3}{\underset{|}{CF}}—CF_2]_n—O—\overset{CF_3}{\underset{|}{CF}}— \quad (2)$$

and n=2-3. This solution was added during a one-hour interval to the stirred reaction mixture, which was maintained at −75° C. by continued cooling. One-half hour following completion of this addition, a 4-ml portion of trifluoroacetic acid was added. The reaction mixture was then allowed to warm to room temperature; then. 50 ml of 1N aqueous sodium bicarbonate was added. The ether layer was separated, and the aqueous layer was extracted with an additional portion of ether. The combined organic solutions were dried over anhydrous magnesium sulfate, concentrated by removal of solvent in a rotary evaporator at a reduced pressure, and heated under vacuum at 150° C. to remove excess dibromobenzene. The residue consisted of the oligomeric ketones (4-bromophenyl)—C(O)—$R_f$, with $R_f$ defined as above, in a yield of 34.4 g (67% of theory).

Similarly, a mixture of methyl esters $CF_3(OCF_2)_nCO_2CH_3$ (n=4-5), derived from the corresponding acyl fluorides described in U.S. Pat. No. 3,692,843 to Resnick, was used in the preparation of oligomeric ketones (4-bromophenyl)—C(O)—$(CF_2O)_nCF_3$, which were obtained in a 60% yield following distillation of the crude product at 76°-78° C. and a pressure of 333-400 Pa.

EXAMPLE 10

Preparation of (4-bromophenyl)perfluoroalkylethers

The mixture of oligomeric ketones (4-bromophenyl)—C(O)—Rf obtained as described above was combined with 35 ml of TCTFE in a stainless-steel pressure tube, to which were then added 8 g of anhydrous HF and 22 g of SF4. The sealed tube was heated and shaken at 180° C. for 18 hours. After the tube was cooled to room temperature, its contents were further diluted with TCTFE. The resulting solution was washed with dilute aqueous sodium bicarbonate, then dried over anhydrous magnesium sulfate. The solvent was removed at a reduced pressure, and the residue was distilled at 76°-88° C./40 Pa to give the oligomeric (4-bromophenyl)—$CF_2$—$R_f$ products in a 70% yield.

Similarly, the oligomeric ketones (4-bromophenyl)—C(O)—$(CF2O)_n CF_3$ (n=4-5), obtained as described above, were converted to the corresponding (4-bromophenyl)—$CF_2$—$(CF_2O)_n CF_3$ products, b.p. 77°-120° C./160 Pa, in a 54% yield.

EXAMPLE 11

Preparation of (4-perfluoroalkyletherphenyl)trimethoxysilanes

In the same manner as described in Example 5, the oligomeric compounds (4-bromophenyl)—$CF_2$—$R_f$, where $R_f$ was as shown in formula (2), were converted to (4-$R_f CF_2$-phenyl)trimethoxysilanes. The crude oligomeric products were partially separated by distillation to give a material consisting primarily of the silane bearing the $R_f$ substituent with n=2 (b.p. 108°-112° C./17 Pa; 57% yield), and a second fraction consisting primarily of the silane bearing the $R_f$ substituent with n=3 (b.p. 112°-117° C./20 Pa; 45% yield).

Similarly, the oligomeric compounds (4-bromophenyl)—$CF_2$—$(CF_2O)_n CF_3$, obtained as described above, where n=4-5, were converted to [4—$CF_3(OCF_2)_n CF_2$—phenyl] trimethoxysilanes. Distillation of the crude oligomeric products afforded two fractions, the first consisting largely of the silane of the above formula with n=4 (b.p. 94°-98° C./120-150 Pa, 53% yield) and the second consisting largely of the silane of the above formula with n=5 (b.p. 84°-88° C./13 Pa; 52% yield).

I claim:

1. An organosilane having the following formula (1):

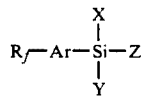

where $R_f$ has at most 18 carbon atoms and is selected from the group consisting of
 (a) perfluoroalkyl groups having at least 4 carbon atoms
 (b) —$[CF_2CF(CF_3)O]_n$—$CF_2$—$CF_2$—$CF_3$, where n is an integer of at least 1;
 (c) —$CF_2$—$(CF_2$—O$)_m$—$CF_3$, where m is an integer of at least 2; and
 (d) —$CH_2$—$C(CF_3)_2$—$CF_2$—$CF_2$—$CF_3$;
Ar is a divalent aromatic radical;
X is selected from the group consisting of
 (e) methyl;
 (f) $R_f$—Ar as defined above;
 (g) halogen atoms selected from the group consisting of chlorine, bromine, and iodine; and
 (h) alkoxy groups; and
each of Y and Z independently is selected from the group consisting of
 (i) halogen atoms selected from the group consisting of chlorine, bromine, and iodine; and
 (j) alkoxy groups.

2. An organosilane of claim 1 wherein the divalent aromatic radical Ar in formula (1) is a radical remaining when two ring hydrogen atoms are removed from an aromatic compound selected from the group consisting of benzene, naphthalene, toluene, xylene, anthracene, furan, pyrrole, and pyridine.

3. An organosilane of claim 1 wherein $R_f$ is a perfluoroalkyl group having more than four carbon atoms.

4. An organosilane wherein at least one of X, Y, and Z is an alkoxy group.

5. An organosilane of claim 4 wherein each alkoxy group has at most four carbon atoms.

6. An organosilane of claim 5 wherein each alkoxy group is selected from the group consisting of methoxy and ethoxy.

7. An organosilane of claim 1 wherein the $R_f$ group has at least 6 carbon atoms.

8. A glass fiber coated with a polysiloxane made by the hydrolysis of an organosilane of claim 1.

9. A glass fiber coated with a polysiloxane obtained by the hydrolysis of an organosilane of claim 6.

* * * * *